US012092627B2

(12) United States Patent
Qian et al.

(10) Patent No.: US 12,092,627 B2
(45) Date of Patent: Sep. 17, 2024

(54) SIGNAL PROCESSING SYSTEM AND METHOD FOR INDUCTIVE OIL ABRASIVE PARTICLE SENSOR

(71) Applicants: Suzhou Renzheng Zhitan Technology Co., Ltd., Suzhou (CN); Nanjing University of Aeronautics and Astronautics, Nanjing (CN)

(72) Inventors: Zhenghua Qian, Suzhou (CN); Mingming Wang, Suzhou (CN); Peng Li, Suzhou (CN); Xianwei Wu, Suzhou (CN); Hairui Liu, Suzhou (CN); Zhi Qian, Suzhou (CN); Qi Li, Suzhou (CN); Zelin Xu, Suzhou (CN)

(73) Assignees: Suzhou Renzheng Zhitan Technology Co., Ltd., Suzhou (CN); Nanjing University of Aeronautics and Astronautics, Nanjing (CN)

( * ) Notice: Subject to any disclaimer, the term of this patent is extended or adjusted under 35 U.S.C. 154(b) by 0 days.

(21) Appl. No.: 18/508,648

(22) Filed: Nov. 14, 2023

(65) Prior Publication Data
US 2024/0159730 A1    May 16, 2024

(30) Foreign Application Priority Data
Nov. 14, 2022  (CN) .......................... 202211420906.X

(51) Int. Cl.
*G01N 33/28* (2006.01)
*G01N 27/02* (2006.01)
(52) U.S. Cl.
CPC ....... *G01N 33/2858* (2013.01); *G01N 27/025* (2013.01)
(58) Field of Classification Search
CPC .................. G01N 33/2858; G01N 27/025
See application file for complete search history.

(56) References Cited

U.S. PATENT DOCUMENTS

| | | | | |
|---|---|---|---|---|
| 6,810,718 B2* | 11/2004 | Wilson | ................ | G01N 23/223 |
| | | | | 702/108 |
| 10,809,164 B2* | 10/2020 | Young | .................... | G01N 21/94 |
| 10,976,277 B2* | 4/2021 | Chana | .................... | G01N 27/18 |

FOREIGN PATENT DOCUMENTS

CN          111504859 A        8/2020

OTHER PUBLICATIONS

CN 202211420906.X, First Office Action, mailed Jan. 31, 2023, pp. 17. (with English translation).

(Continued)

*Primary Examiner* — Elias Desta
(74) *Attorney, Agent, or Firm* — Getech Law LLC; Jun Ye

(57) ABSTRACT

A signal processing system and method for inductive oil abrasive particle sensor, comprising a sensor, an excitation signal generator, an analog signal processing circuit, a MCU signal acquisition module and a computer signal processing module is disclosed. The sensor is provided with two groups of induction coils, the excitation signal generator generates excitation signals and drives the excitation coils of the sensor to output induction signals containing abrasive particle information, and the analog signal processing circuit receives the induction signals output by the sensor and demodulates and amplifies the induction signals. The signal processing system of the sensor applied to online monitoring of oil abrasive particles is simple in structure and convenient to apply, has a complete signal statistics and monitoring interface, and can be used to effectively monitor the size, concentration and other information of the metal abrasive particles in oil in real time.

3 Claims, 6 Drawing Sheets

(56) References Cited

OTHER PUBLICATIONS

CN 202211420906.X, Notification to Grant, mailed Feb. 19, 2023, pp. 2. (with English translation).
CM 202211420906.X, First Office Action, mailed Jan. 31, 2023, pp. 17. (with English translation).
Xianwei Wu, et al., "A New Inductive Debris Sensor Based on Dual-Excitation Coils and Dual-Sensing Coils for Online Debris Monitoring", Sensor, vol. 21, Nov. 2021, 14 pages.
Liu Kailun, "Design of a New Oil Debris Sensor", A Thesis in Aeronautical Engineering, Engineering Technology II of Chinese Master's Theses Full-text Database (CMFD), Issue 2, 2020, 71 pages.
Feng Wenpeng, "Design and Research of Online Wearparticle Monitoring System for Lubricating Oil", Information Technology of Chinese Master's Theses Full-text Database (CMFC), Issue 2, 2014, 67 pages.

* cited by examiner

SIGNAL PROCESSING SYSTEM AND METHOD FOR INDUCTIVE OIL ABRASIVE PARTICLE SENSOR

TECHNICAL FIELD

The present invention belongs to the technical field of online monitoring of the running state of mechanical equipment, and in particular relates to a signal processing system and method for inductive oil abrasive particle sensor.

BACKGROUND

With the development of modern industrial technology, there are higher requirements for the stability of mechanical equipment, and the wear of mechanical parts is one of the main factors affecting the stability, reliability and service life of mechanical equipment. The metal abrasive particles resulting from wear flow with lubricating oil in mechanical equipment. The information such as the quantity, quality, composition, and shape of the abrasive particles is closely related to the wear and operating status of the mechanical parts. Therefore, the size, quantity and other parameters of metal abrasive particles in lubricating oil can be detected to evaluate the wear status of mechanical equipment, and to judge the operating status and fault status of mechanical equipment.

Online monitoring of oil abrasive particles does not need to take oil samples, but relies on a sensor integrated in the lubricating oil system for data collection, and abrasive particles are monitored in real time based on a specific measurement principle, boasting three characteristics of continued monitoring, real-time monitoring and synchronization of monitored equipment operating status with analysis conclusions. Therefore, online detection of oil abrasive particles is the main research interest of lubricating oil system detection.

Online detection methods mainly include the following six categories: optical method, capacitance method, resistance method, ultrasonic method, X-ray method and induction method. Among them, the inductive metal abrasive particle detection method has the advantages of simple structure, convenient installation, no influence of oil quality, and the feasibility of distinguishing ferromagnetic metal particles from non-ferromagnetic metal particles. However, in current engineering applications, sensors with larger pipe diameters still have problems such as low sensor sensitivity, serious signal noise interference, and lack of complete online signal monitoring system.

SUMMARY

The present invention provides a signal processing system and method for inductive oil abrasive particle sensor, aiming to solve the above existing problems.

The purpose of the present invention is achieved by a signal processing system and method for inductive oil abrasive particle sensor, and the signal processing system includes excitation signal generator module, analog signal processing circuit module, MCU signal acquisition module and computer signal processing program module; the excitation signal generator module generates an excitation signal to drive the sensor excitation coil; the analog signal processing circuit module demodulates and amplifies the sensor output signal; the MCU signal acquisition module is used to collect the processed induction signal, and transmits the signal to the computer; the computer signal processing program module is used for identifying and counting the induction signal data transmitted to the computer, and displaying the monitoring information of abrasive particles through the monitoring panel.

Further, the excitation signal generator module includes microcontroller, digital synthesis signal generator, filter amplitude modulation circuit and power amplifier circuit.

Further, the MCU is used to send the control command to the digital synthesis signal generator, and the frequency control word in the control command is used to determine the frequency of the output signal of the digital synthesis signal generator;

The digital synthesis signal generator utilizes direct digital synthesis (DDS) technology, after receiving the control command, synthesizes the digital signal sequence of the required frequency, and then outputs the analog sinusoidal signal after A/D conversion and low-pass filtering;

The filter amplitude modulation circuit processes the signal output by the signal synthesizer with a high-pass filter to filter out the DC offset component in the signal;

The power amplifier circuit amplifies the signal after filter amplitude modulation through power amplifier, so that it drives the sensor excitation coil to generate a magnetic field of sufficient strength.

Further, the analog signal processing circuit module includes RMS conversion circuit, filter amplitude modulation circuit, differential amplifier circuit and post amplifier circuit.

Further, the RMS conversion circuit receives the signals output by the two groups of induction coils of the sensor, and demodulates the two induction signals respectively according to the principle of RMS detection;

The filter amplitude modulation circuit is high-pass filter, which filters the two signals that have undergone RMS detection, filters out the DC offset, and leaves the induction signal containing abrasive particle information;

The differential amplifier circuit differentially amplifies two filtered signals, and since the abrasive particles pass through the two groups of coils in different time sequences, the differentially amplified abrasive particle induction signals are synthesized into the sinusoidal signal waveform of one cycle;

The post amplifier circuit further filters and amplifies the differentially amplified signal to improve the signal-to-noise ratio.

Further, the MCU signal acquisition module includes matching and driving circuit, A/D conversion circuit, MCU acquisition circuit and serial communication circuit.

Further, the matching and driving circuit is the input voltage matching circuit of the A/D converter and driving circuit of the successive approximation A/D converter and is used for receiving the output signal of the analog signal processing circuit, and scaling the amplitude of the signal, so that the voltage of the signal falls within the voltage range of the input signal of the A/D converter;

The A/D conversion circuit and the MCU acquisition circuit carry out A/D conversion of the signal through the A/D converter inside the MCU, and collect signals into the MCU;

The serial communication circuit transmits the collected signal data to the computer through serial communication.

Further, the computer signal processing program module includes a computer communication program, a signal identification and statistics program, and an abrasive particle data monitoring program.

Further, the computer communication program is used to receive signal data transmitted to the computer serial port and store the signal in the data queue;

The signal identification and statistics program retrieves the signal data in the data queue in segments, uses the state machine program to identify the induction signal when there are abrasive particles in the signal data, and classifies the signal according to ferromagnetic and non-ferromagnetic categories and different size intervals;

The abrasive particle data monitoring program is a monitoring panel of the signal processing system, through which the information of abrasive particles in oil can be monitored online in real time.

The present invention also provides a signal processing method for inductive oil abrasive particle sensor, comprising the following steps:

Step S1: Calculate the frequency value of the required excitation signal, and use the MCU to send the control command to the digital synthesis signal generator. After receiving the command, the digital synthesis signal generator outputs a sinusoidal signal according to the requirements, and drives two excitation coils of the sensor after filter amplitude modulation and power amplification, and the two induction coils output the corresponding induction signals at this time;

Step S2: After performing RMS detection, filter amplitude modulation, differential amplification and filter amplification on the two received induction coil output signals through the analog signal processing circuit, output the induction signal of the metal abrasive particles;

Step S3: Use the MCU signal acquisition module to perform A/D conversion of the output induction signals of the metal abrasive particles and collect them into the MCU, and transmit the signal data to the computer through the serial communication circuit.

Step S4: Identify and count the signal data transmitted to the computer through the computer signal processing module, and display the abrasive particle monitoring information through the monitoring panel.

Compared with the prior art, the beneficial effect of the present invention is as follows: the present invention discloses a signal processing system and method for inductive oil abrasive particle sensor. For the current inductive oil abrasive particle detection sensor, the signal processing system of the sensor applied to online monitoring of oil abrasive particles is simple in structure and convenient to apply, has a complete signal statistics and monitoring interface, and can be used to effectively monitor the size, concentration and other information of the metal abrasive particles in oil in real time.

EMBODIMENTS

Figure 1:
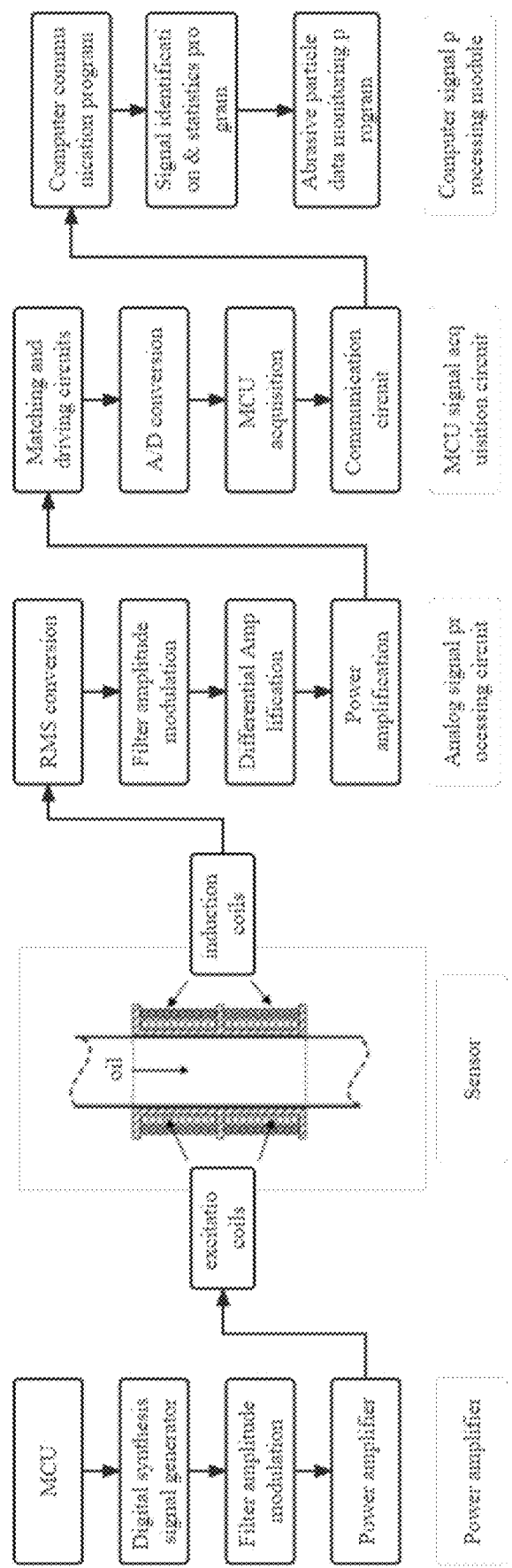
FIG. 1 is a schematic structural diagram of the signal processing system of the present invention.

In order to make the purposes, technical solutions, and advantages of the present invention more fully apparent, further details of the present invention are set forth with reference to the drawings and embodiments. It should be appreciated that the specific embodiments described herein are merely illustrative of the present invention and are not intended to be limiting of the present invention.

In the description of the present application, it is to be understood that the terms "length", "width", "upper", "lower", "front", "back", "left", "right", "vertical", "horizontal", "top", "bottom", "inside", "outside", and other presentations relating to orientation or positional relationship is based on the orientation or positional relationship shown in the attached figure, and is merely for the convenience of the description of the present invention or a simplified description, rather than indicating or implying that the device or component referred to herein has a specific orientation or is manufactured or operated in a specific orientation, which shall not be construed as limitations on the present invention. Unless otherwise stated, "a plurality of" means two or more in the description of the present invention.

By referring to FIGS. 1-6, the present invention provides a technical solution: a signal processing system for inductive oil abrasive particle sensor, including sensor, excitation signal generator, analog signal processing circuit, MCU signal acquisition module and computer signal processing module.

Among them, the sensor has two groups of induction coils. The excitation signal generator generates an excitation signal and drives the sensor excitation coil to output the induction signal containing abrasive particle information. The analog signal processing circuit receives the induction signal output by the sensor, and demodulates and amplifies the induction signal; the MCU signal acquisition module collects the processed induction signals and transmits the induction signals to the computer; the computer signal processing module identifies and counts the induction signal data transmitted to the computer, and displays the abrasive particle monitoring information through the monitoring panel.

Specifically, the excitation signal generator includes MCU, digital synthesis signal generator, first filter amplitude modulation circuit and power amplifier circuit.

The MCU sends the control command to the digital synthesis signal generator, and the frequency control word in the control command is used to determine the frequency of the output signal of the digital synthesis signal generator; the digital synthesis signal generator receives the control command, synthesizes the digital signal sequence, and outputs the analog sinusoidal signal after A/D conversion and low-pass filtering; the first filter amplitude modulation circuit processes the signal output by the digital synthesis signal generator with a high-pass filter to filter out the DC offset component in the signal; the power amplifier circuit amplifies the signal after filter amplitude modulation through power amplifier, and drives the sensor to excite the coil to generate magnetic field;

The analog signal processing circuit includes RMS conversion circuit, second filter amplitude modulation circuit, differential amplifier circuit and post amplifier circuit;

The RMS conversion circuit receives the induction signals output by two groups of induction coils of the sensor, and demodulates the two induction signals separately according to the principle of RMS detection; the second filter amplitude modulation circuit is high-pass filter, which filters the two induction signals that have undergone RMS detection, filters out the DC offset, and leaves the induction signal containing abrasive particle information; the differential amplifier circuit differentially amplifies two filtered induction signals, and since the abrasive particles pass through the two groups of coils in different time sequences, the differentially amplified induction signals are synthesized into the sinusoidal signal waveform of one cycle; The post amplifier circuit further filters and amplifies the differentially amplified signal to improve the signal-to-noise ratio.

The MCU signal acquisition module includes matching and driving circuit, A/D conversion circuit, MCU acquisition circuit and serial communication circuit.

The matching and driving circuit is the input voltage matching circuit of the A/D converter and driving circuit of the successive approximation A/D converter and is used for receiving the output signal of the analog signal processing circuit, and scaling the amplitude of the signal, so that the voltage of the signal falls within the voltage range of the input signal of the A/D converter; the A/D conversion circuit and the MCU acquisition circuit carry out A/D conversion of the signal through the A/D converter inside the MCU, and collect signals inside the MCU; the serial communication circuit transmits the collected signal data to the computer through serial communication.

The computer signal processing module includes communication program, signal identification and statistics module, and abrasive particle data monitoring module.

The communication program receives signal data transmitted to the computer serial port and store the signal in the data queue; the signal identification and statistics module retrieves the signal data in the data queue in segments, identifies the induction signal when there are abrasive particles in the signal data, and classifies the signals according to ferromagnetic and non-ferromagnetic categories and different size intervals; the abrasive particle data monitoring module is used for real-time online monitoring and display of abrasive particles in oil.

Figure 2:
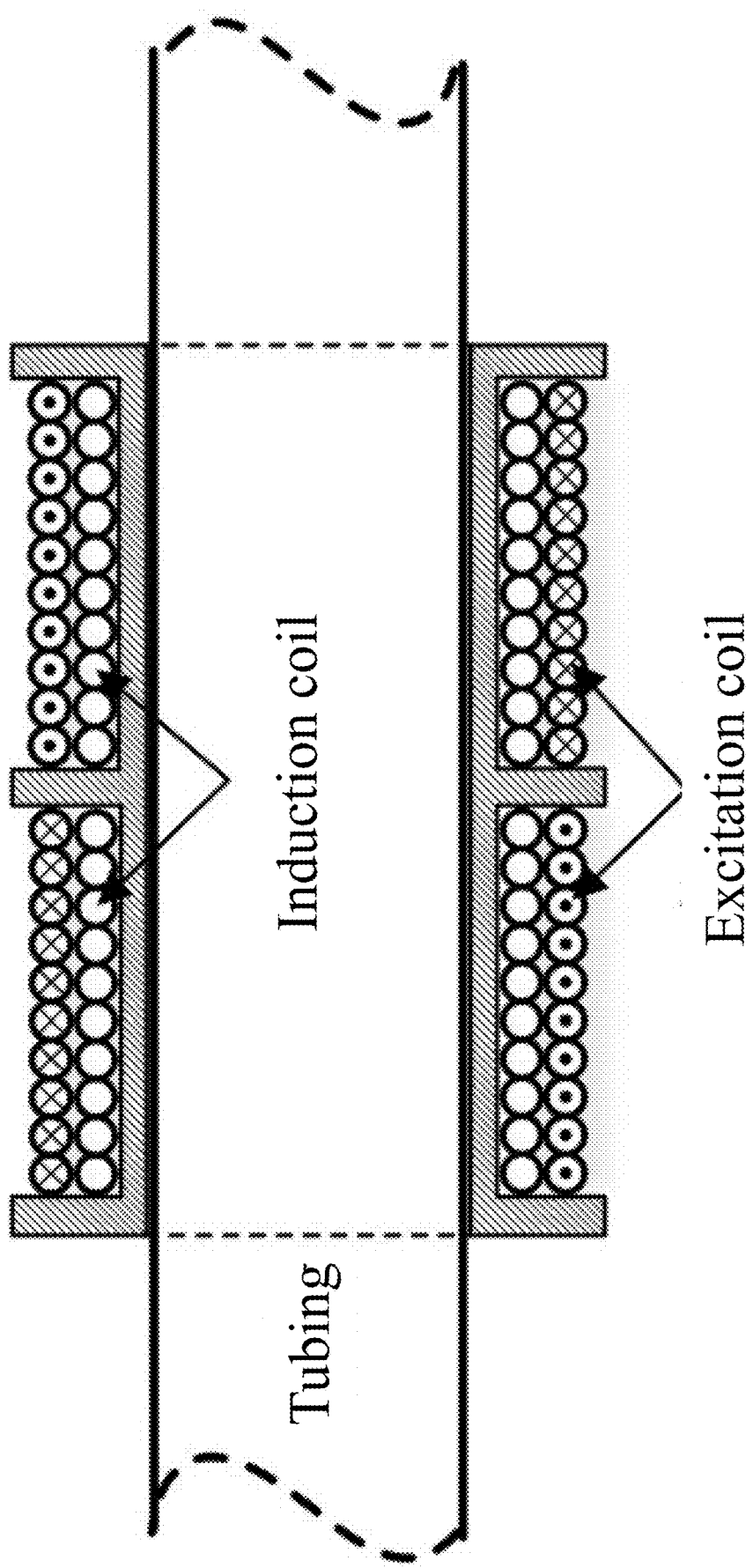
FIG. 2 is a schematic structural diagram of the sensor.

The present invention is based on a dual-excitation dual-inductive oil abrasive particle sensor, as shown in FIG. 2, and consists of two groups of excitation coils and induction coils wound on ceramic tubes.

When a high-frequency AC signal is passed into the excitation coil, an alternating magnetic field is generated inside the excitation coil. At this time, the induction coil is affected by the magnetic field and produces an alternating induced electromotive force. When no metal particles pass through the coil, the RMS of the alternating induced electromotive force remains unchanged. When ferromagnetic metal particles pass through the coil, the maximum alternating induced electromotive force increases under the magnetization effect and eddy current effect of the metal particles in the alternating magnetic field.

When non-ferromagnetic metal particles pass through, under the eddy current effect of the non-ferromagnetic metal particles in the alternating magnetic field, a magnetic field opposite to the excitation magnetic field is generated, the RMS of the alternating induced electromotive force decreases, and the induced electromotive force opposite to that when the ferromagnetic metal particle passes through is output.

The output signal can be regarded as the double sideband amplitude modulation signal of the carrier signal, and the information related to the metal abrasive particles can be obtained by processing the sensor output signal with the demodulation circuit.

As shown in FIG. 1, a signal processing system for inductive oil abrasive particle sensor includes excitation signal generator module, analog signal processing circuit module, MCU signal acquisition module and computer signal processing program module; among them, the excitation signal generator module generates the excitation signal to drive the sensor excitation coil; the analog signal processing circuit module demodulates and amplifies the sensor output signal; the MCU signal acquisition module is used to collect the processed induction signal, and transmits the signal to the computer; the computer signal processing program module is used for identifying and counting the induction signal data transmitted to the computer, and displaying the monitoring information of abrasive particles through the monitoring panel.

Figure 3:
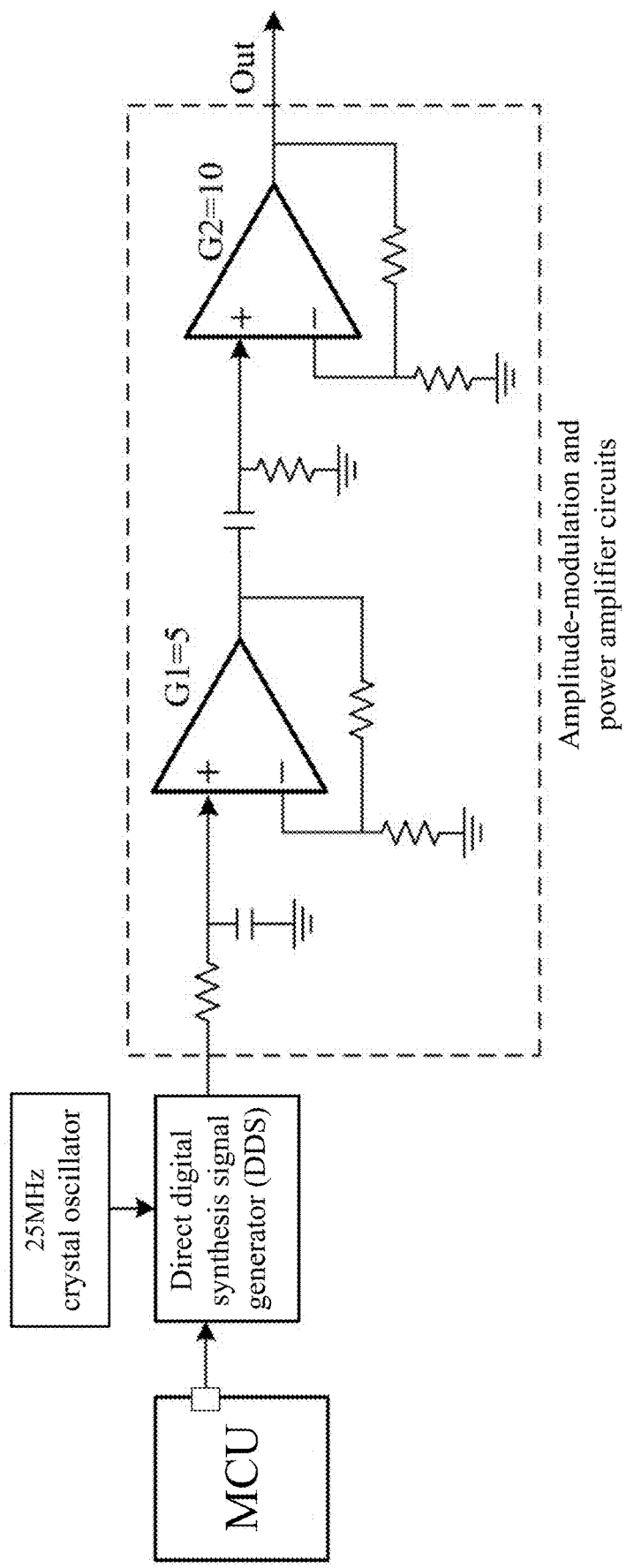
FIG. 3 is a schematic diagram of the excitation signal generator module.

FIG. 3 is a schematic diagram of the excitation signal generator, including MCU, digital synthesis signal generator, filter amplitude modulation circuit and power amplifier circuit.

First, calculate the frequency control word according to the frequency of the required excitation signal, and use the MCU to send a control command containing the frequency control word to the digital synthesis signal source; then, after the digital synthesis signal generator receives the control command, synthesize sinusoidal signals of the required frequency based on a 25 MHz crystal oscillator; finally, amplify the synthesized sinusoidal signal 5 times by amplitude modulation and 10 times by power amplification and then output an excitation signal to drive the sensor excitation coil.

Figure 4:
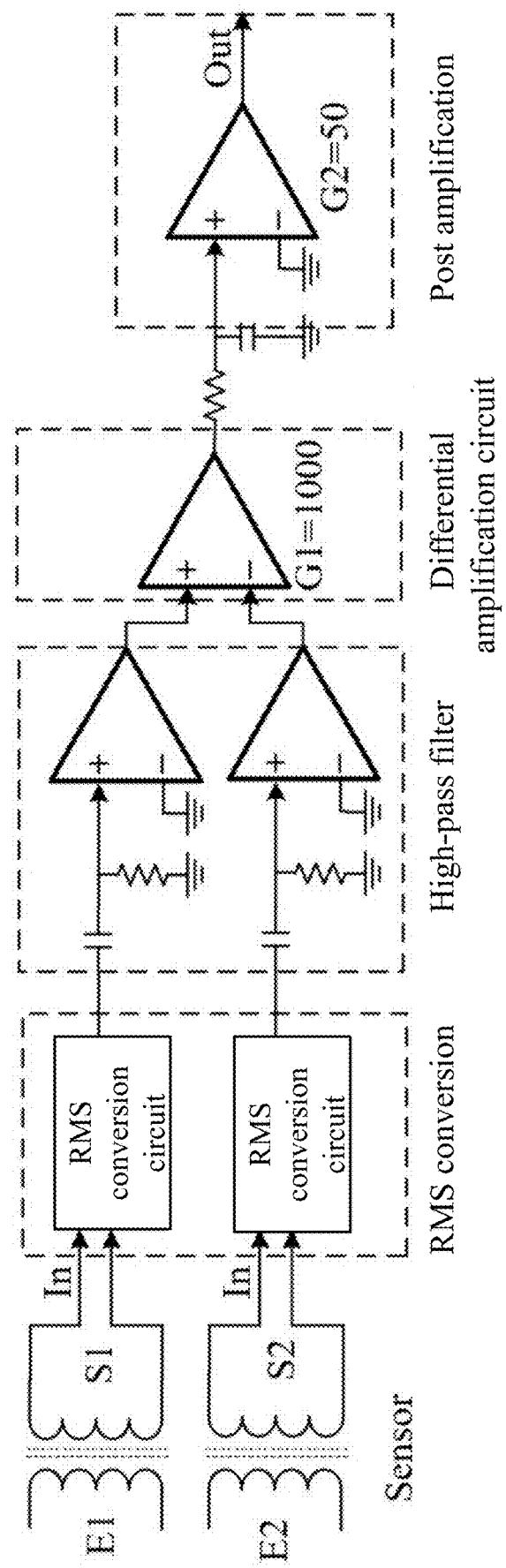
FIG. 4 is a schematic diagram of the analog signal processing circuit module.

FIG. 4 is a schematic diagram of the analog signal processing circuit, including RMS conversion circuit, filter amplitude modulation circuit, differential amplifier circuit and post amplifier circuit.

First, the RMS conversion circuit uses AD637 to design the circuit, receives the output signals of the two groups of induction coils S1 and S2 of the sensor, and demodulates the two signals respectively according to the principle of RMS detection; secondly, the filter amplitude modulation circuit is a high-pass filter used to filter the two signals after RMS detection, filters out the DC offset, and leave the induction signal with wear particle information; then, the differential amplifier circuit performs differential processing on the two signals filtered and amplifies them by 1,000 times; since the time sequence of the abrasive particles passing through the two groups of coils is different, the differentially amplified abrasive particle induction signal synthesizes the sinusoidal signal waveform of one cycle; finally, the post amplifier circuit further filters and amplifies the differentially amplified signal by 50 times, thus improving the signal-to-noise ratio.

Figure 5:
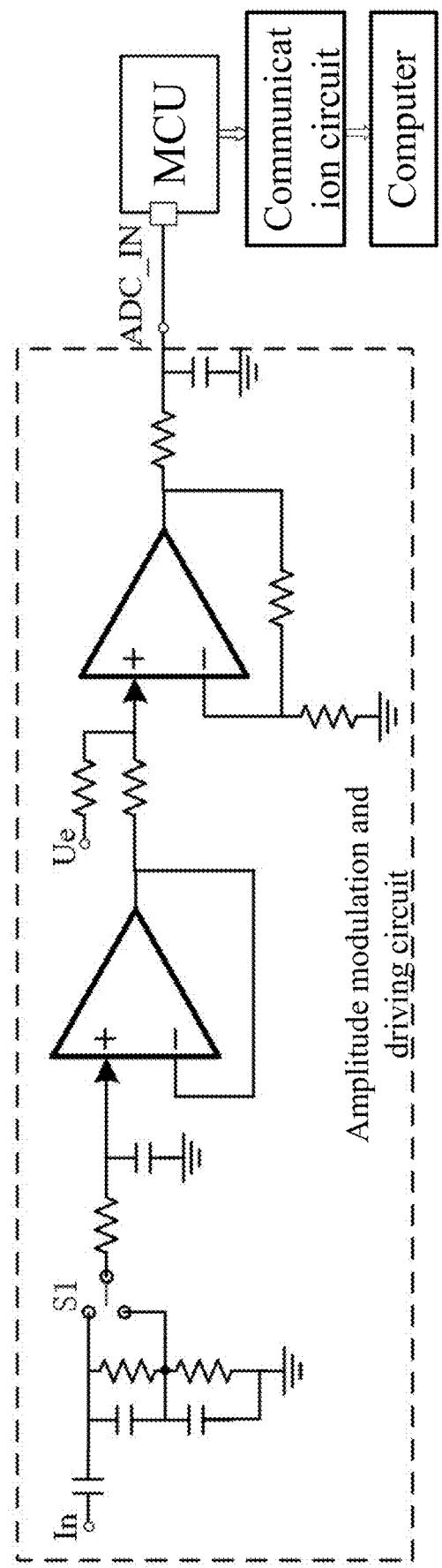
FIG. 5 is a schematic diagram of the MCU signal acquisition module.

FIG. 5 is a schematic diagram of the MCU signal acquisition module, including matching and driving circuits, A/D conversion circuit, MCU acquisition circuit and serial communication circuit.

The matching and driving circuit is the input voltage matching circuit of the A/D converter and the successive approximation A/D converter driving circuit. Its function is to receive the output signal of the analog signal processing circuit, and first attenuate the signal within the range of ±10V to ±2.5V, and then superimpose the signal with a DC component of 2.5V and attenuate it to $3/5$ of the original signal, so that the voltage of the signal falls within the input signal voltage range of the A/D converter, i.e., 0-3V, and then the MCU acquisition circuit uses the A/D converter inside the MCU to convert the signal to A/D, collects the signal inside the MCU, and uses the serial communication circuit to transmit the collected signal data to the computer through serial communication.

Figure 6:
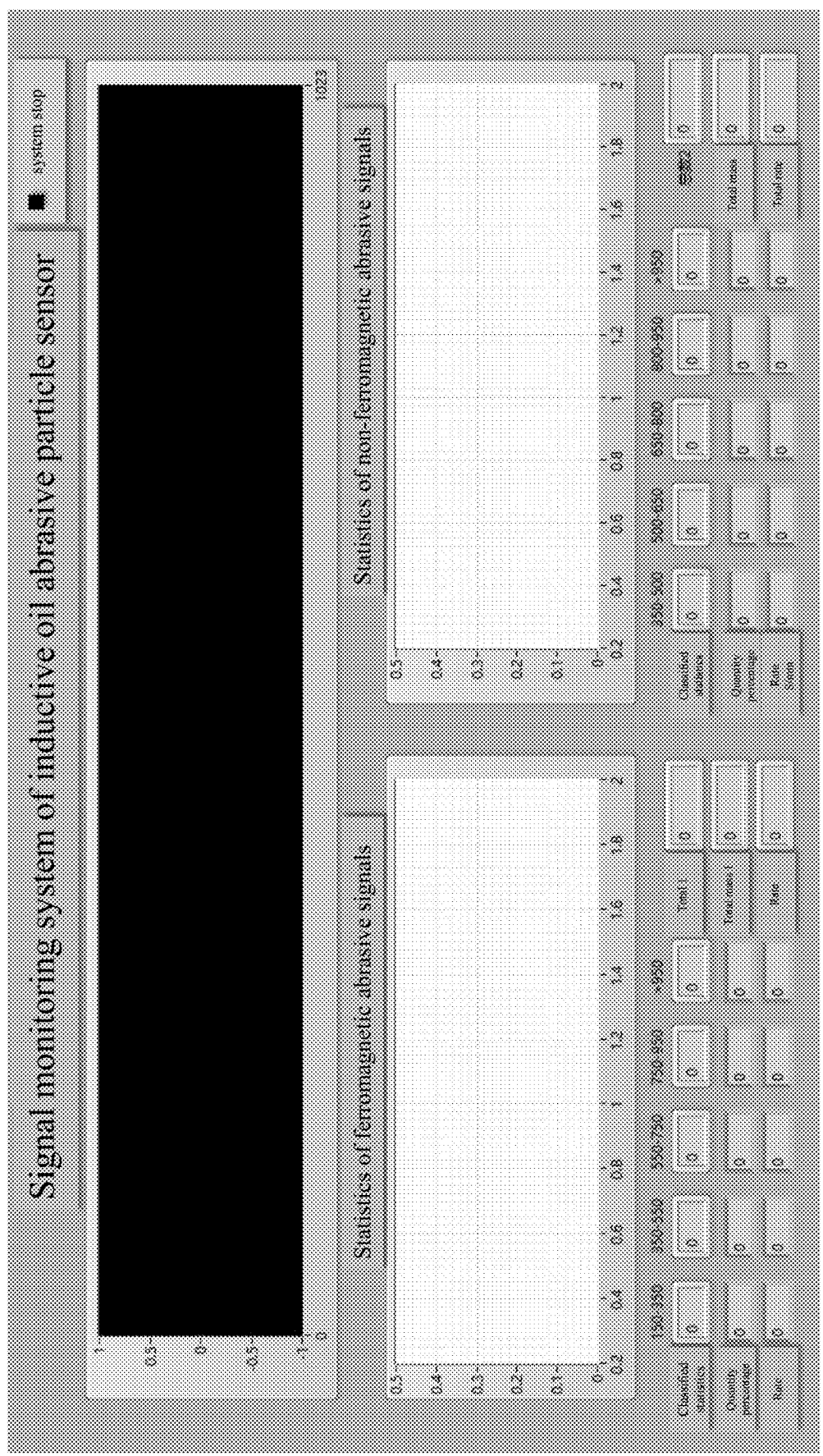
FIG. 6 is a schematic diagram of the abrasive particle information monitoring interface of the computer signal processing program module.

FIG. 6 is a schematic diagram of the abrasive particle information monitoring interface of the computer signal processing program module. The computer signal processing program includes computer communication program, signal identification and statistics program, and abrasive particle data monitoring program.

First, the computer communication program receives the signal data transmitted to the serial port of the computer, and stores the signal in the data queue; then, the signal identification and statistics program calls the signal data in the data queue in segments, and uses the state machine program to identify the induction signal of abrasive particles in signal data; after the signal amplitude and the sequence of peak and valley values are measured, the signals are classified and counted according to ferromagnetic and non-ferromagnetic categories and different size intervals; finally, the abrasive particle data monitoring program is the monitoring panel of the signal processing system, and the information of abrasive particles in oil is monitored in real time through the monitoring panel. The monitoring information includes the real-time display of the induction signal, and the number, percentage of quantity, rate and other information of each size segment are counted respectively according to ferromagnetic and non-ferromagnetic categories.

The above is only the preferred embodiments of the present invention, and is not intended to limit the scope of the present invention. Any modification, equivalent substitution and improvement made within the spirit and principles of the present invention shall be covered by the scope of protection of the present invention.

The invention claimed is:

1. A signal processing system for inductive oil abrasive particle sensor, comprising:
 a sensor with two groups of induction coils;
 an excitation signal generator, wherein the excitation signal generator generates an excitation signal and drives sensor excitation coils to output an induction signal containing abrasive particle information;
 an analog signal processing circuit, wherein the analog signal processing circuit receives the induction signal output by the sensor, and demodulates and amplifies the induction signal;
 a microcontroller unit (MCU) signal acquisition module, wherein the MCU signal acquisition module collects the processed induction signal, and transmits the induction signal to a computer;
 a computer signal processing module, wherein the computer signal processing module identifies and counts the induction signal data transmitted to the computer, and displays the abrasive particle information through a monitoring panel;
 the excitation signal generator includes a microcontroller unit (MCU), a digital synthesis signal generator, a first filter amplitude modulation circuit, and a power amplifier circuit;
  the MCU sends a control command to the digital synthesis signal generator, and
 a frequency control word in the control command is used to determine the frequency of the signal output by the digital synthesis signal generator;
  the digital synthesis signal generator receives the control command, synthesizes a digital signal sequence, and outputs an analog sinusoidal signal after Analog-to-Digital (A/D) conversion and low-pass filtering;
  the first filter amplitude modulation circuit processes the signal output by the digital synthesis signal generator with a high-pass filter to filter out the Direct Current offset component in the signal;
  the power amplifier circuit amplifies the signal after filter amplitude modulation, and drives the sensor to excite the excitation coils to generate a magnetic field;
 the analog signal processing circuit includes a Root Mean Square (RMS) conversion circuit, a second filter amplitude modulation circuit, a differential amplifier circuit and a post amplifier circuit;
  the RMS conversion circuit receives the induction signals output by the two groups of induction coils of the sensor, and demodulates the two induction signals separately according to a principle of RMS detection;
  the second filter amplitude modulation circuit is a high-pass filter, which filters the two induction signals that have undergone RMS detection, filters out the Direct Current offset, and leaves the induction signals containing abrasive particle information;
  the differential amplifier circuit differentially amplifies two filtered induction signals, and the differentially amplified induction signals are synthesized into a sinusoidal signal waveform of one cycle;
  the post amplifier circuit further filters and amplifies the differentially amplified signal to improve the signal-to-noise ratio;
 the MCU signal acquisition module includes a matching and driving circuit, an A/D conversion circuit, a MCU acquisition circuit and a serial communication circuit;
  the matching and driving circuit is an input voltage matching circuit of an A/D converter and a driving circuit of a successive approximation A/D converter and is used for receiving the output signal of the analog signal processing circuit, and scaling the amplitude of the signals, so that the voltage of the signals falls within the voltage range of the input signal of the A/D converter;
  the A/D conversion circuit and the MCU acquisition circuit carry out A/D conversion of the signals through the A/D converter inside the MCU, and collect signals into the MCU; and
  the serial communication circuit transmits the collected signal data to the computer through serial communication.

2. The signal processing system for inductive oil abrasive particle sensor of claim 1, wherein the computer signal processing module includes a communication module, a signal identification and statistics module, and an abrasive particle data monitoring module.

3. The signal processing system for inductive oil abrasive particle sensor of claim 2, wherein the communication module receives the signal data transmitted to a computer serial port, and stores the signal in a data queue;
 the signal identification and statistics module retrieves the signal data in the data queue in segments, identifies the induction signal when there are abrasive particles in the signal data, and classifies the signal according to ferromagnetic and non-ferromagnetic categories and different size intervals; and
 the abrasive particle data monitoring module is used for real-time online monitoring and display of abrasive particles in oil.

* * * * *